United States Patent [19]

Schram

[11] Patent Number: 4,673,512

[45] Date of Patent: Jun. 16, 1987

[54] PARTICLE SEPARATION

[75] Inventor: Cornelius J. Schram, Bedford, England

[73] Assignee: Internationale Octrooi Maatschappij "Octropfa" BV, Rotterdam, Netherlands

[21] Appl. No.: 751,951

[22] Filed: Jul. 5, 1985

[30] Foreign Application Priority Data

Jul. 6, 1984 [GB] United Kingdom ............... 8417240

[51] Int. Cl.$^4$ ........................ B01D 17/06; C02F 1/36
[52] U.S. Cl. .................................. 210/748; 436/177; 435/261; 209/1; 204/157.15
[58] Field of Search ............ 210/748, 635, 656, 198.2; 209/1; 55/15, 277; 436/177; 435/261; 204/157.15

[56] References Cited

U.S. PATENT DOCUMENTS

| 2,215,484 | 9/1940 | St. Clair | 55/277 |
| 3,837,147 | 9/1976 | Brunnee | 55/277 |
| 4,055,491 | 10/1977 | Porath-Furedi | 210/748 |
| 4,280,823 | 7/1981 | Szonntagh | 209/1 |
| 4,475,921 | 10/1984 | Barmatz | 55/15 |
| 4,523,682 | 6/1985 | Barmatz et al. | 209/1 |

FOREIGN PATENT DOCUMENTS 1442610 4/1969 Fed. Rep. of Germany ...... 210/748

Primary Examiner—Benoît Castel
Attorney, Agent, or Firm—Cushman, Darby & Cushman

[57] ABSTRACT

The separation of different types of particulate matter in a carrier liquid is obtained by using an ultrasonic standing wave and relying on the different acoustic responses of the different particle types. By varying the acoustic energy propagation cyclically a more effective separation rate can be obtained, with a more readily attracted particle type being subjected to a further discrimination step in each cycle. The cyclical energy variation may be in the intensity of the standing wave, e.g. using suppression means, and/or the velocity of the standing wave relative to the liquid medium, e.g. using phase control means.

6 Claims, 7 Drawing Figures

PARTICLE SEPARATION

BACKGROUND OF THE INVENTION

This invention relates to the separation of different types of particulate matter in a liquid medium using an ultrasonic standing wave propagated through the medium. It relates particularly, although not exclusively, to a method and a means for chromatography.

In one of its main aspects, the invention is concerned with the separation of biological particles, which term is used here to include a range of particulate matter from macromolecules —e.g. globular proteins —through viruses, bacteria and yeasts, to tissue cells —e.g. plant cells, animal cells and aggregates —but it can also be employed on many finely divided inorganic and organic materials, including siliceous minerals such as clays.

In chemical chromatography, the isolation of chemical components from a mixture for their identification is achieved relying on very small quantities of any one component. That even very complex mixtures can be represented safely by a small sample, so that the column is not overloaded, is due to the uniformity of any given molecular species, individual molecules differing only in features such as isomeric form and isotopic composition to which the separation process is quite insensitive.

It has been proposed in U.S. Pat. No. 4 280 823 to provide a chromatographic column to analyse a sample of red blood cells which is entrained in a gas flow through the column while an ultrasonic transducer at one end of the column directs its output onto a reflector at the opposite end, its frequency and its distance from the reflector being so matched that a standing wave is produced by the interaction of the emitted and reflected waves. It is described in that disclosure how the nodes of the standing wave can function in the same way as a series of filter plates of a chemical chromatograph to promote separation of the constituents of the sample as it moves along the column.

However, biological particles such as cells are much less uniform, individual members of a group differing in size, age, metabolic state and so forth. Moreover, many of these variations within a group are those to which an acoustic separation is acutely sensitive. There are difficulties therefore in applying chromatographic methods using ultrasonic energy to the analysis of large populations of particles and to the detection of fine distinctions of various groups by having each represented by adequate cell populations.

The method disclosed in U.S. Pat. No. 4 280 823 would have at best a limited utility, because to obtain substantial and sufficiently complete separation of any mixed group of biological particles a very large column length is dictated. But apart from the bulk and cost resulting from any substantial increase in size, there is a limit to the maximum column length that can be employed, owing to the attenuation of an ultrasonic wave that occurs with distance and that restricts the length over which the incident and reflected wave energies are sufficiently well matched to form a predominating standing wave. It may be mentioned here that, apart from this major problem, the method disclosed in U.S. Pat. No. 4 280 823 has further disadvantages because of the difficulty of handling biological particles in a gaseous environment, in particular as regards difficulty of control and prevention of damage to or transformation of the particles.

The problem of separating large populations of particles, particularly biological particles may be even more severe if acoustic energy methods are to be employed for a bulk separation process rather than simply the analysis of a very small sample.

It may be expected, for example, that problems would be encountered if an apparatus such as is described in GB No. 2 089 498A were to be used for the separation of large quantities of particles in a mixed population. In that apparatus a flow of liquid in a conduit passes through a zone in which ultrasonic transducers at opposite sides of the conduit are driven with a controlled phase angle between their driving signals so as to establish a standing wave pattern that moves across the conduit, along the common axis of propagation of the two transducers. Particles carried along by the flow through the conduit enter the standing wave transverse to its axis and the acoustic energy is effective only over a very short distance along the length of the conduit. The extent to which particles can be differently displaced along the standing wave is correspondingly severely limited. This limitation, coupled with the difficulties of achieving the separation of groups of non-uniform particles discussed above, means that the apparatus described in GB No. 2 089 498A would have no application to the separation of biological particles.

It is an object of the present invention to provide a method in which the separation of particle types having different acoustic properties can be more effectively performed.

SUMMARY OF THE INVENTION

According to one aspect of the invention there is provided a method of separating different type of particles in which an ultrasonic standing wave is propagated in a liquid medium and there is relative motion between the medium and the standing wave, the different types of particles being differently influenced by the acoustic energy of the standing wave and/or the Stokes or drag forces of the liquid medium, characterised in that the acoustic energy propagation is varied cyclically, whereby the different particle types are caused to move at different rates with respect to the standing wave and are thereby progressively separated.

The method may be performed by varying the intensity of the standing wave to effect said cyclical variation of the acoustic energy propagation. In one particular way of putting this method into effect, the standing wave is alternatively suppressed and reestablished without disturbing the phase continuity of electrical driving signals producing the acoustic energy.

In another method of effecting said variation of the ultrasonic wave propagation, the standing wave is caused to move at a varying rate. It is also possible to combine such cyclic variations of the standing wave intensity and velocity.

According to another aspect of the invention, there is provided apparatus for the separation of different types of particles in a liquid medium, comprising means for propagating an ultrasonic standing wave in the medium and for generating a relative movement between the medium and the standing wave, the apparatus further comprising means for varying cyclically the acoustic energy propagation in order that different types of particles having different responses to the acoustic energy of the standing wave and/or the Stokes or drag forces generated by relative movement between the particles and the liquid medium are caused to move at different rates with respect to the standing wave and are thereby progressively separated.

The invention will be described by way of example with reference to the accompanying drawings.

DESCRIPTION OF THE PREFERRED EMBODIMENTS

Figure 1:
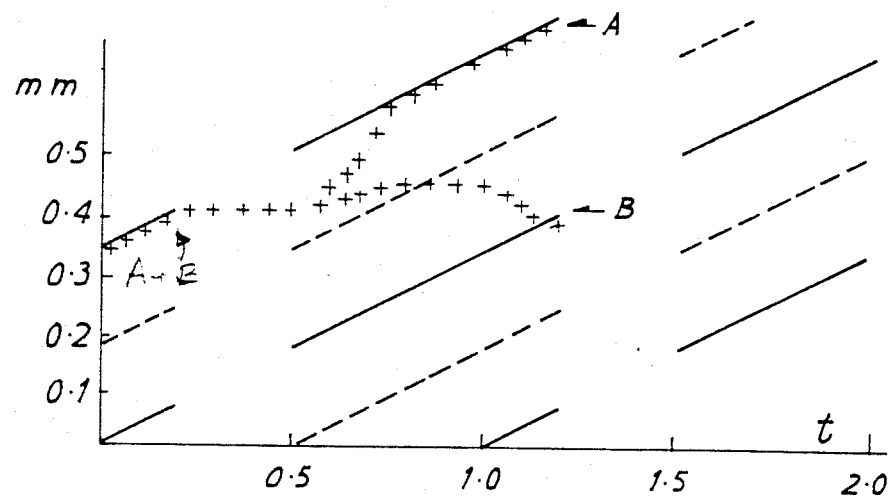
FIGS. 1 and 2 illustrate schematically the separation of different types of particles in a liquid medium through which a periodically suppressed standing wave is propagated.

FIG. 1 illustrates the propagation of an ultrasonic standing wave having a wavelength of 0.7 mm, and thus an internodal distance of 0.35 mm at a constant velocity of one internodal distance per second. (Such an internodal distance corresponds, for instance, with a 2MHz wave in water at room temperature). This propagation in the liquid medium occurs in such a manner that there is uniform relative movement along the axis of propagation of the standing wave between the standing wave and the liquid. Distance in mm along the axis of propagation is plotted against a time base (t) in seconds and the graph represents the moving nodes (full lines) and antinodes (broken lines) having a velocity of 0.35 mm/sec relative to the liquid. FIG. 1 also shows interruption of the standing wave in a 1 second cycle with the wave being propagated for 0.7 sec and then suppressed for 0.3 sec, but the movement between the standing wave and the liquid corresponds to that of a continuously propagated standing wave with uniform relative motion, giving a 1 second internodal period (wavelength divided by relative velocity).

If a mixed population of particles suspended in the liquid is subjected to the acoustic energy of the standing wave, at a given relative velocity between the wave and the liquid/any particles uninfluenced by the acoustic energy will remain static, some that are only weakly influenced will oscillate about a mean position as each node passes, while others more strongly influenced will move with the nodes. (It should be mentioned here that the factors determining whether any given particle type tends to be attracted to the nodes or the antinodes are unclear, but this lack of theoretical understanding is not material to the present invention and where the context permits the term "nodes" can be read to include both nodes and antinodes).

Particles of two different types A and B are shown in FIG. 1 at the beginning of the separation process both attached to a node of the standing wave and thus moving relative to the liquid with the standing wave, but the response to the acoustic forces and therefore the strength of attachment to the node is greater for type A than for type B. When the standing wave is suppressed (as first occurs at 0.2 sec as shown in FIG. 1) the particles are left static in the liquid. Very small particles e.g. of the order of microns, have very little inertia and in a liquid medium both types A and B will stop moving virtually immediately the wave is suppressed.

When the standing wave is re-established at 0.5 sec, with the nodes displaced a distance proportional to the period of interruption, particles A and B are now positioned between the node on which they were originally held and the following antinode. An A type particle, being acted on more strongly by the acoustic forces, will move towards the original node at a speed faster than the node is itself moving relative to the liquid and will thus quickly be reattached to the node. A B type particle will also move towards the original node but is less strongly attracted, to the extent that its velocity is less than the relative velocity between the standing wave and the liquid. The particle B thus soon finds itself at the following antinode, where the attraction forces of the original node and its following node cancel each other out, and the particle then quickly comes under the influence of the approaching following node to move towards it. The particle B soon attaches itself to the following node, so that the two particle types are now separated by an internodal distance. The standing wave is again suppressed and the cycle repeated, whereupon the particle A attaches again to the original node and the particle B falls back a further internodal distance. As this process is continued, the particles become separated by as many internodal distances as there are interruptions in the propagation of the standing wave. In general, the interruption cycle time will be of the same order as the internodal period, so that particles A and B will be presented with a large number of successive opportunities to increase their separation over a relatively small time period.

In the system shown in FIG. 1 the progress of the nodes can be related to a standing wave moving with uniform velocity. For any given internodal period, the period during which the standing wave is suppressed determines the position relative to the wave pattern that the particles occupy when the wave is re-established. Clearly, it is necessary for the period of suppression to have an interval significantly less than half the internodal period in order that the particle A finds itself between a node and the following antinode (it can also comprise any integral number of internodal periods, but there will not be any advantage generally in so extending the period), so that it may be advanced with the standing wave while the particle B falls back to a following node. With the suppression period limited to a fraction of the internodal period, those particles that have been carried forwards on a node will find themselves starting again near that node; the particles should not be so close to the original node, however, that the attraction forces on a particle B are strong enough to draw it also towards that node.

As regards the period of propagation of the standing wave in each cycle, the simplest method maintains the standing wave long enough to ensure that both types of particle attach themselves to spaced nodes. The conditions in each interruption of the standing wave can thus be relatively precisely repeated. It will be noted, however, that since the particle A reattaches itself to the original node before the particle B falls back to the succeeding node, the period of propagation can be shortened to a time sufficient to allow that reattachment of the particle A, leaving the particle B somewhere in the region of the following antinode.

This has particular significance in handling high concentrations of particles in which groups are often formed, and in other conditions in which the cycle should be repeated as frequently as possible to achieve optimum separation. For example, it can be expected that some particles of one group will be entrained by concentrations of particles of the other group, or if the process is carried out in a standing wave which is not entirely uniform in energy density, with the minor lateral disturbances that will always be present this process allows continual redistribution of particles with a final degree of separation truly reflecting the average conditions in the column.

Figure 2:
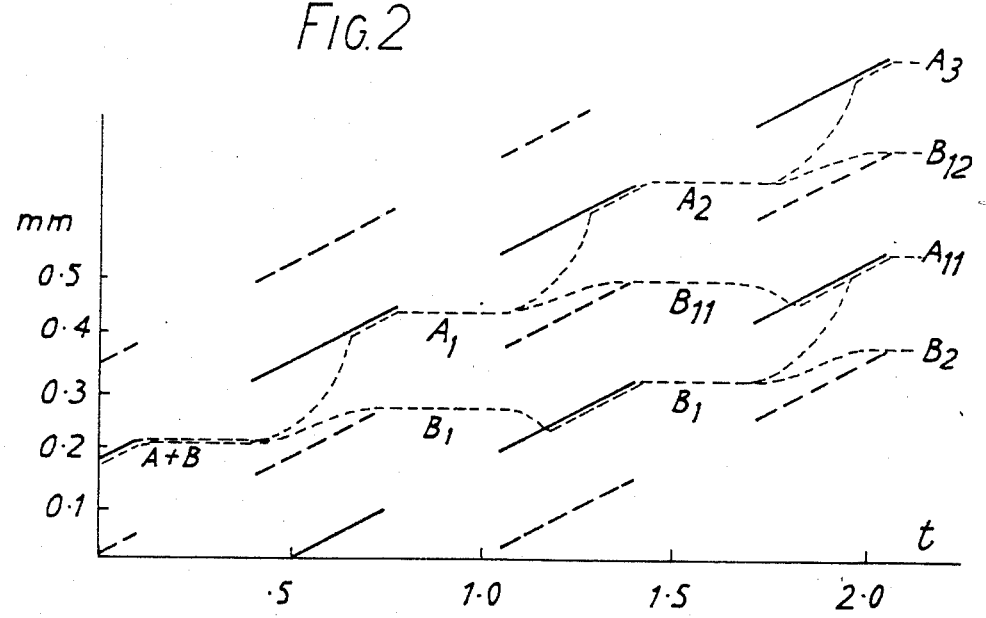

FIG. 2 illustrates a process in which the conditions are generally the same as in FIG. 1, except that the propagation period has been reduced to 0.35 sec, giving an 0.65 sec cycle. At the end of the first cycle a group $A_1$ of particles enriched with particle A is reattached to the original node, while a group $B_1$ of particles enriched with particle B lies in the region of the following antinode. When the wave is re-established in the second cycle, group $A_1$ is again in the same position relative to the nodal array as in the first cycle and another B-rich fraction $B_{11}$ falls back to the following antinode, so that the group $A_2$ attaching itself to the original node in the third cycle has a further reduced content of group B particles, while the group $B_1$ is exposed to no selection process in this second cycle and merely joins the following node. In the third cycle, the group $A_2$ has more B type particles removed in group $B12$ leaving a further purified group $A_3$ of A particles to reattach itself to the original node in the following cycle. In the third cycle the group $B_1$ is also subjected to another separation process since it starts the cycle in a corresponding position to that of the original mixture in the first cycle, and an A-rich fraction $A_{11}$ is drawn from it, leaving a purer group $B_2$ of B particles.

By varying the propagation period, the suppression period and cycle time in relation to the internodal period there is scope for adjusting the degree of discrimination and the rate of working required. It is possible, for example, to shorten the cycle still further than is described in FIG. 2, since it will be possible to ensure continuing separation when the two groups are separated by less than half an internodal distance in a period of propagation. In particular it will not normally be necessary to ensure that the more strongly influenced group reattaches to the original node before the standing wave is suppressed. By keeping the cycle time to the minimum practical period possible, the process can be highly selective because of the very large number of separation stages that can be contained over a very short distance in the liquid.

Figure 3:
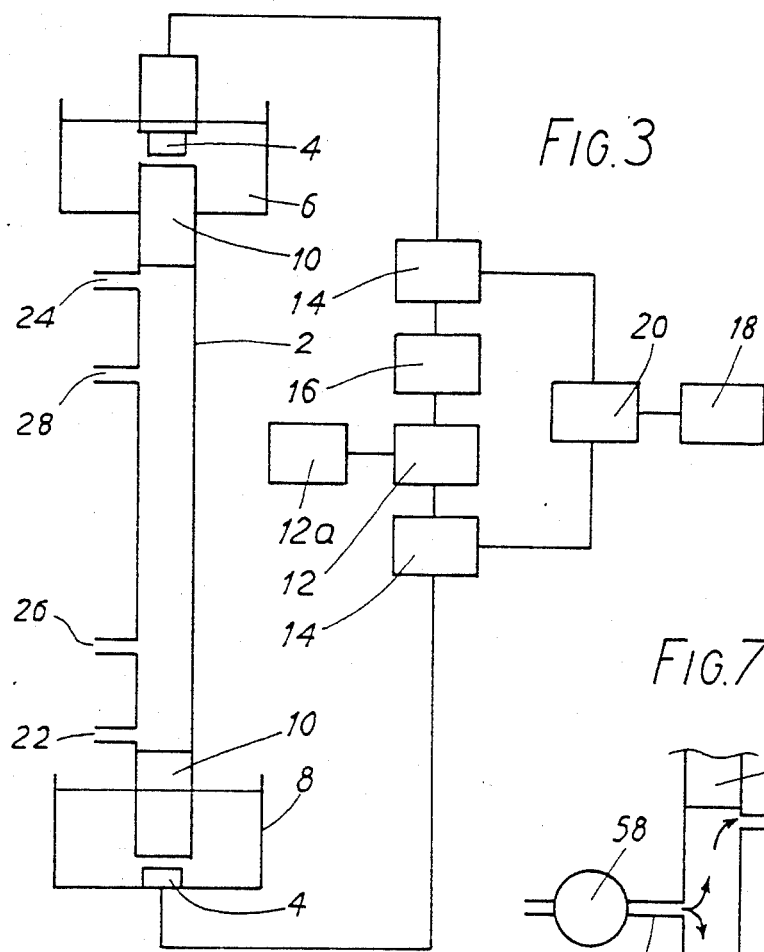
FIG. 3 is a schematic illustration of an apparatus for performing the separation process described in FIGS. 1 and 2.

FIG. 3 illustrates schematically an apparatus in which the processes of FIGS. 1 and 2 may be performed. A liquid-filled column 2 has a standing wave propagated in it by opposed ultrasonic transducers 4 at opposite ends of the column. Opposite ends of the column are immersed in liquid baths 6, 8, but are sealed from the contents of the baths by end plugs 10 transparent to the ultrasonic energy, and the transducers 4 are disposed in the liquid of the baths, aligned with each other so that the axis of propagation of ultrasonic energy from each is coaxial with the central axis of the column. The transducers are driven from an oscillator, 12, having a power supply 12a, through respective amplifiers 14. A phase control unit 16 between the oscillator 12 and one amplifier produces a relative phase shift between the outputs of the two transducers so that the standing wave resulting from the interference of the two coaxially propagated ultrasonic outputs from the transducers is caused to move along the column in a direction and at a rate determined by the phase control. A power supply 18 for the two amplifiers 14 is controlled by switching means 20 so that the energisation of both transducers can be switched on and off jointly to produce the cyclic suppression of the standing wave already described.

The column has inlet and outlet ports 22, 24 for a carrier liquid adjacent opposite ends of the liquid-filled space between the plugs. Sample injection ports 26, 28 are disposed between the carrier liquid ports one adjacent each port.

In the one mode of operation, a continuous slow flow of liquid is established between the liquid ports 22, 24 and a mixed sample of two particle types is injected into the column through the port 26 adjacent to the liquid inlet port 22. The standing wave is caused to move in the direction from the inlet port 22 to the outlet port 24 and, as described with reference to FIGS. 1 and 2, the types of particles are progressively separated and spaced apart as they travel towards the opposite end of the column. By closing the liquid outlet port 24 and opening the adjacent sample port 28 when the separated group of the first type of particle approaches the further end of the column, the different groups of particles can be collected sequentially as they arrive at the sample port over different intervals of time.

Even more simply, by relying solely on the motion generated by the standing wave, it is possible to use a liquid column with only one entry port at one end and a pair of opposed exit ports at the other end. The entry port is utilised to inject a sample into a column and a flushing liquid flow between the two ports at the opposite end of the column will sweep out one group of particles that have been moved to that end by the moving wave, the rest of the particles remaining at the entry end uninfluenced by the acoustic energy. By choice of different ultrasonic frequencies and/or energy intensities different fractions can be separated from a mixture.

Figure 4:
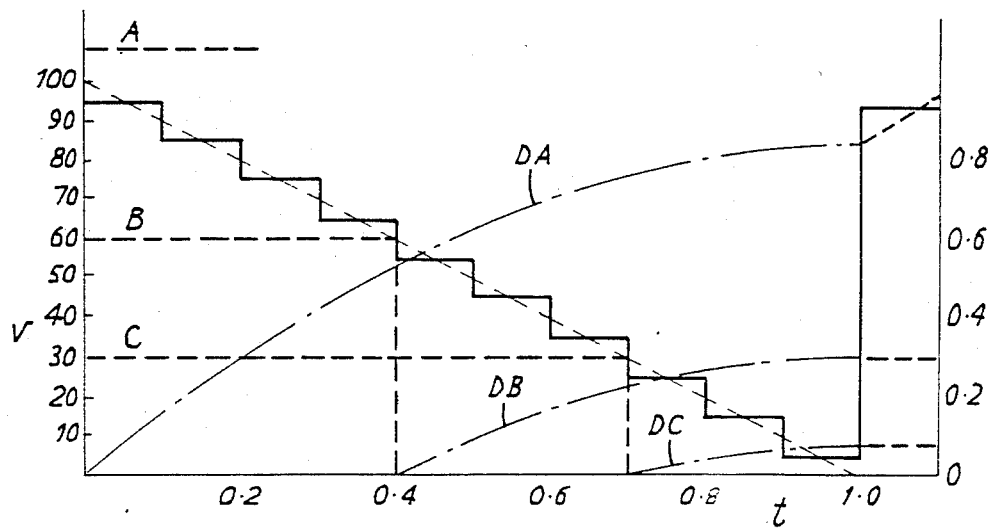
FIG. 4 illustrates schematically the separation of different types of particles in a liquid medium through which a standing wave is propagated with variable rate of movement.

A further process according to the invention is illustrated in FIG. 4, in which the standing wave is caused to move through the liquid medium at a variable rate. In this example, a cyclical series of stepped phase changes are introduced between the two opposed transducers, the figure showing a 1 sec. cycle with ten stepped stages, the wave velocity (v) being indicated on the left-hand vertical scale in mm/minute from a maximum wave velocity of 95 mm/min to a minimum of 5 mm/min in 0.1 sec steps. The number of steps can be increased and in the extreme case the linear variation indicated by the broken line in FIG. 4 illustrates a continuous linear rate of change from 100 mm/min to 0 over the 1 sec cycle. The total distance travelled by a node of the standing wave pattern is plotted in curve DA against the vertical scale of distance (d) in mm indicated on the right-hand side of the figure; thus over one complete cycle the travel distance totals 0.83 mm.

To understand how variation of the standing wave velocity brings about separation of particle types that are differently influenced by the standing wave, it will be understood from the earlier examples that the progressive movement of any particle with the movement of the standing wave will have a limiting velocity depending on the strength of response of the particle to the standing wave, since that response must be used to overcome the Stokes forces on the particle. If the velocity range in the regime illustrated in FIG. 4 is matched to the responses of the different types of particles in a sample, only the most strongly influenced particles are entrained by the wave at its highest velocity relative to the carrier liquid medium and will move at the same mean speed as that of the standing wave. Less strongly influenced particles will only be entrained by the standing wave when its velocity falls below some critical value less than the maximum velocity. FIG. 4 illustrates curves DA, DB and DC of the distance travelled by three different particles, A, B and C with different responses to the standing wave such that the critical or transitional velocity for particle A is 110 mm/min, that for particle B is 60 mm/min and for particle C is 30 mm/min. particle A, having a critical velocity greater than the maximum velocity of the wave remains attached to a node throughout and moves with the node a distance of 0.83 mm in one cycle. Particle B is unable to be entrained by the standing wave until the wave velocity falls below 60 mm/min, at 0.4 sec into the cycle, and its movement over the remaining part of the cycle totals 0.3 mm. particle C can similarly only be entrained after 0.7 sec and travels only 0.075 mm by the end of the cycle.

Continuing repetition of the cycle progressively improves the separation into groups and increases the spacing between separated groups of particles. The efficiency of the process is relatively independent of the cycle frequency; although shorter cycle times are preferred it may be found that at frequencies of the order of 4 MHz a cycle time substantially shorter than one second cannot provide sufficiently long periods of energisation to displace particles significantly towards a node.

Figure 5:
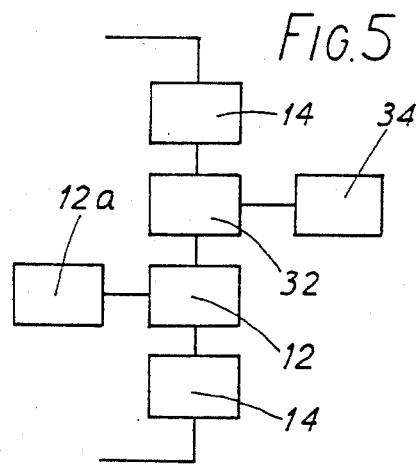
FIG. 5 is a fragmentary illustration of a modification of the apparatus of FIG. 4 to operate the separation process of FIG. 4.

FIG. 5 illustrates in block diagram form the modified driving circuit for the transducers to produce the variable velocity pattern shown in FIG. 4.

The transducers may be set up with a liquid column in the same way as is shown in FIG. 3. The oscillator 12 now drives one of the two amplifiers 14 through a phase lock unit 32, capable of providing a chosen phase difference between its input and output, and a phase shift control 34 that varies that chosen phase difference in accordance with a desired wave velocity profile. Further details of such a method of control of the standing wave appear in co-pending application Ser. No. 751,952 by Michael W. B. Lock filed simultaneously herewith, the contents of which are incorporated herein by reference.

Figure 6:
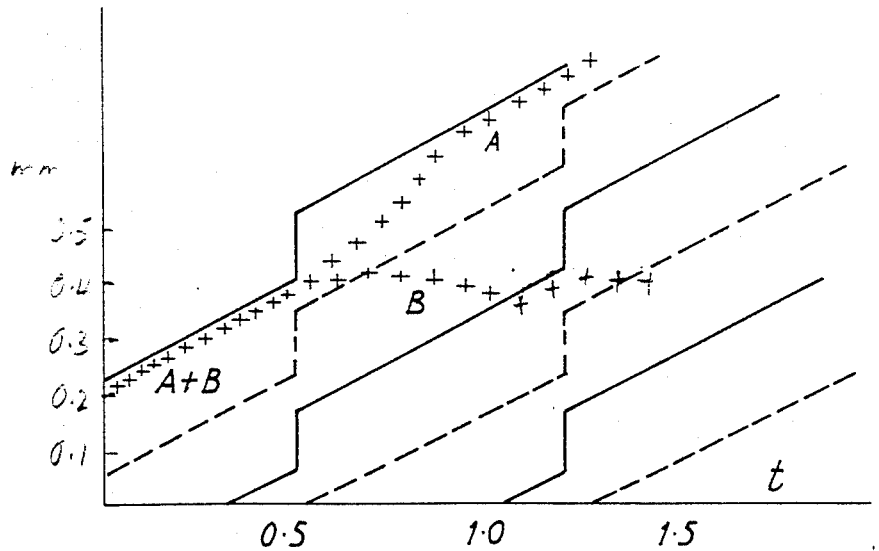
FIG. 6 is another schematic illustration of the separation of different types of particles employing phase changes in the propagation of the standing wave to produce stepped displacements.

By use of a phase shift system it is also possible to establish a regime in which, in place of the periods of wave suppression shown in FIGS. 1 and 2 there is a more or less instantaneous change of phase giving an equivalent displacement of the nodes in a substantially shorter cycle time. This is illustrated in FIG. 6. It may be required in such a regime to allow for the inertia of the particles, although this is small, if relatively abrupt and large changes of force are imposed on them.

Figure 7:
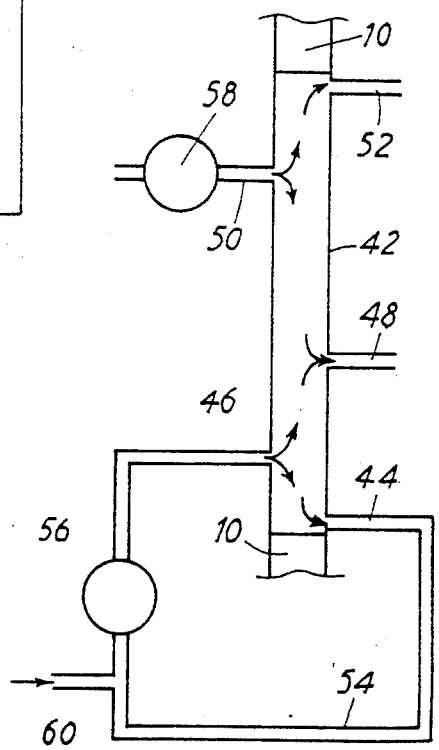
FIG. 7 is a further fragmentary illustration of another modification of the apparatus of FIG. 3 to operate a continuous separation process.

It has already been mentioned that the invention is not only applicable to chromatography, and an example of its use in a continuous separation process will now be given with reference to FIG. 7, which shows a modified liquid column 42 that can replace the column 2 of FIG. 3. The means for generating an ultrasonic standing wave are not illustrated, but a variable intensity wave of the character described with reference to FIG. 4, can be employed, using the means described with reference to FIG. 5.

The column 42 has a series of ports 44, 46, 48, 50, 52 spaced along its length between the end plugs 10. The ports 44, 46 are connected to a circulatory conduit 54 through which liquid is drawn by a pump 56 so that liquid flows through the column from port 46 to port 44. Liquid is also pumped into the column through port 50 by a further pump 58 to exit through ports 48 and 52. The particulate matter to be separated is introduced into the circulatory conduit 54 through a port 60. The pumping rates are such that the liquid velocity is greater from port 46 to port 44 than it is from port 50 to port 48, while there is a low velocity flow in the opposite direction from port 46 to port 48.

At the region opposite the port 46 particles sufficiently influenced by the standing wave are picked up by the nodes which move towards the port 50 as the relative velocity between the standing wave and the liquid changes from the relatively high value between the ports 46 and 44 to a relatively low value between the ports 46 and 48. Above the port 48, there is a counterflow of liquid so that its velocity relative to the standing wave increases again, but it is not so great as to cause all the particles to be shed from the standing wave. Thus, particles so strongly attached to the nodes as to resist the Stokes forces will continue up the column with the standing wave but the remainder will leave the column with the flow through the port 48. That group of particles continuing upwards past the port 48 is removed from the column by the flow through the port 52.

In this method of operation two distinct counterflow systems are established in two successive portions of the column, so that of the particles drawn off from the circulating flow, two separate groups are formed. It will be clear from this example that the apparatus may include further liquid inlet and/or outlet ports along the length of the column to establish a series of different velocity regimes, thereby to increase the number of fractions into which a mixed group of particles is separated in a continuous process.

I claim:

1. In a method of separating different types of particles in which an ultrasonic standing wave having an axis of propagation, and a series of nodes transverse to the axis is propagated in a liquid medium and there is relative motion between the medium and the standing wave, the different types of particles being differently influenced by the acoustic energy of the standing wave and/or the Stokes or drag forces of the fluid medium, the improvement comprising cyclically varying the energy propagation of said standing wave so that the different particle types are caused to move at cyclically varying rates in the direction of the axis of propagation and thereby progressively separating said different particle types while remaining suspended in the liquid medium.

2. A method according to claim 1 wherein substantially instantaneous phase changes are introduced between two acoustic energy outputs which interact to produce the moving standing wave, thereby superimposing additional intermittent movements onto the substantially continuous movement of the standing wave.

3. A method according to claim 1 wherein the standing wave is subjected to cycles of velocity variation in each of which the velocity is varied unidirectionally between a maximum and a minimum rate of movement for the standing wave.

4. In a method of separating different types of particles in which an ultrasonic standing wave having an axis of propagation, and a series of nodes transverse to the axis is propagated in a liquid medium and there is relative motion between the medium and the standing wave, the different types of particles being differently influenced by the acoustic energy of the standing wave and/or the Stokes or drag forces of the fluid medium, the improvement comprising cyclically varying the energy propagation by varying the intensity of said standing wave so that the different particle types are caused to move at different rates in the direction of the axis of propagation different particle types while remaining suspended in the liquid medium.

5. A method according to claim 3 wherein the standing wave is periodically suppressed and re-established.

6. A method according to claim 5 wherein said suppression and re-establishment of the standing wave is performed without disturbing the phase continuity of electrical driving signals producing the acoustic energy.

* * * * *